(12) United States Patent
Wuchinich

(10) Patent No.: US 7,374,552 B2
(45) Date of Patent: May 20, 2008

(54) LONGITUDINAL-TORSIONAL ULTRASONIC TISSUE DISSECTION

(76) Inventor: David G. Wuchinich, 431 Hawthorne Ave., Yonkers, NY (US) 10705

( * ) Notice: Subject to any disclaimer, the term of this patent is extended or adjusted under 35 U.S.C. 154(b) by 48 days.

(21) Appl. No.: 11/196,362

(22) Filed: Aug. 3, 2005

(65) Prior Publication Data

US 2005/0264139 A1 Dec. 1, 2005

Related U.S. Application Data

(63) Continuation of application No. 09/833,109, filed on Apr. 11, 2001, now Pat. No. 6,984,220.

(60) Provisional application No. 60/196,357, filed on Apr. 12, 2000.

(51) Int. Cl.
*A61B 17/20* (2006.01)
(52) U.S. Cl. .......................................... 604/22; 606/169
(58) Field of Classification Search .................. 604/22; 606/166, 170, 167, 169; 310/328, 333
See application file for complete search history.

(56) References Cited

U.S. PATENT DOCUMENTS

| | | | |
|---|---|---|---|
| 3,526,219 A | | 9/1970 | Balamuth |
| 3,589,363 A | * | 6/1971 | Banko et al. ................. 604/22 |
| 4,038,571 A | | 7/1977 | Hellenkamp |
| 4,063,557 A | | 12/1977 | Wuchinich |
| 4,136,700 A | | 1/1979 | Broadwin |
| 4,281,987 A | | 8/1981 | Kleesattel |
| 4,504,264 A | | 3/1985 | Kelman |
| 4,750,902 A | | 6/1988 | Wuchinich |
| 5,176,677 A | | 1/1993 | Wuchinich |
| D345,784 S | | 4/1994 | Hood |
| 5,318,570 A | * | 6/1994 | Hood et al. ................... 606/99 |
| 5,811,909 A | | 9/1998 | Wuchinich |
| 6,077,285 A | * | 6/2000 | Boukhny ..................... 606/169 |
| 6,984,220 B2 | * | 1/2006 | Wuchinich ..................... 604/22 |

OTHER PUBLICATIONS

*Ultrasonic Engineering*; Alan E. Crawford; Butterworths Scientific Publications; 1955; pp. 252-253.
*Ultrasonic Cutting*; L.D. Rozenberg; Consultants Bureau; 1964; pp. 56-57.
*Ultrasonic Engineering*; Julian R. Frederick; John Wiley & Sons, Inc.; 1964; pp. 86-101.
*Sources of High-Intensity Ultrasound*; vol. 2; Part VI; Chapter 5; L.D. Rozenberg; Plenum Press; 1969; pp. 173-183.
*Surgical Technology International III*; Joseph E. Amaral; 1994; pp. 155-161.

* cited by examiner

*Primary Examiner*—Kevin C. Sirmons
*Assistant Examiner*—Catherine N. Witczak
(74) *Attorney, Agent, or Firm*—Connolly, Bove

(57) ABSTRACT

An ultrasonic tissue dissection system providing combined longitudinal and torsional motion of tips, together with irrigation and aspiration, for improved cutting of resistant biological tissue. The system permits the use of common and inexpensive electro-mechanical transducers for the production of such motion through the use of longitudinal-torsional resonators.

14 Claims, 3 Drawing Sheets

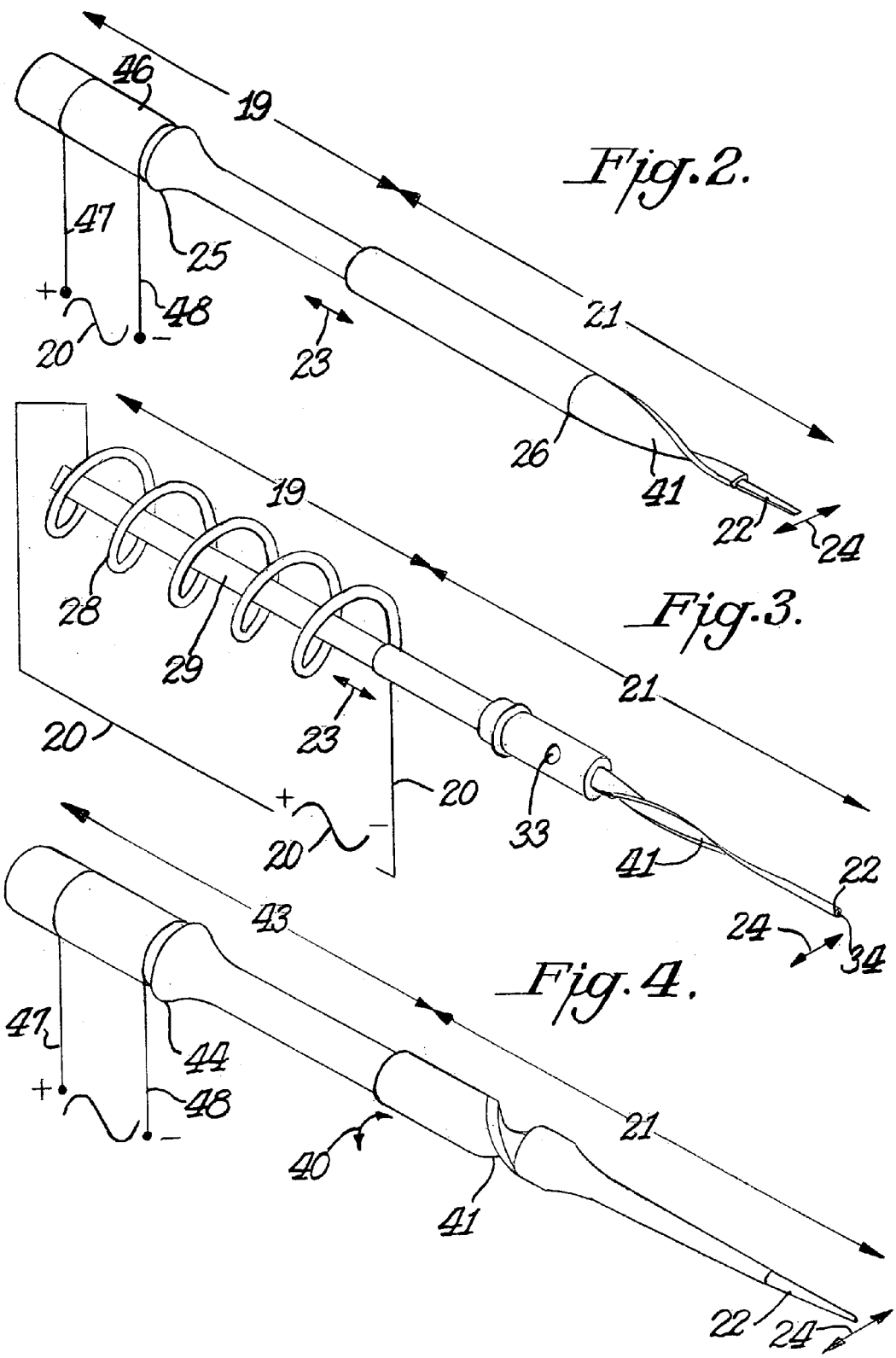

LONGITUDINAL-TORSIONAL ULTRASONIC TISSUE DISSECTION

CROSS REFERENCE TO RELATED APPLICATION

This application is a continuation of U.S. patent application Ser. No. 09/833,109 filed Apr. 11, 2001, now U.S. Pat. No. 6,984,220 which is based on provisional application No. 60/196,357 filed Apr. 12, 2000. The details of both applications are fully incorporated herein by reference thereto.

BACKGROUND

1. Field of Invention

This invention describes the use of mechanical resonant longitudinal-torsional vibration to dissect biological tissue.

2. Description of Prior Art

The use of ultrasonic vibration to separate tissue was disclosed by Balamuth (U.S. Pat. No. 3,526,219) in 1970 who showed a variety of surgical instruments equipped with tips for different applications in the dissection of biological tissue. His devices provided motion either parallel also known as longitudinal, motion or perpendicular, known as parallel motion, to tissue surface. Kelman and Banko (U.S. Pat. No. 3,589,363) disclosed in 1971 apparatus and methods for dissecting and simultaneously aspirating tissue with a device that provided longitudinal tip contacting motion. Broadwin and Weiss (U.S. Pat. No. 4,136,700) later developed an aspirating ultrasonic tissue dissector that utilized transverse tip motion. Kelman (U.S. Pat. No. 4,504,264) and the Wuchinich (U.S. Pat. No. 5,176,677) patented ultrasonic dissectors that utilized, in addition to ultrasonic longitudinal tip motion, transverse tip ultrasonic motion with motor driven rotation to enhance tissue removal. Wuchinich (U.S. Pat. No. 4,750,902) also patented apparatus for the endoscopic dissection of tissue, combining the use of longitudinal ultrasonic vibration with aspiration, irrigation, telescopic vision and electro-cauterization.

Chief among the limitations of ultrasonic tissue dissection has been its feeble ability to separate collagenous tissue, bone and other connective or structurally supportive tissue. However, because ultrasonic vibration offers precise control and very little thermal and collateral damage, attempts have been repeatedly made to improve its performance on tissue otherwise resistant to its effect. Wuchinich shows one such invention (U.S. Pat. No. 5,176,677) for using transverse ultrasonic motion in combination with rotation to cut collagenous tissue such as cartilage and the meniscus.

All of the devices and methods that have been disclosed have not accomplished the object of rapid, precise removal of tissue normally resistant to ultrasonic dissection. Furthermore, although instruments that incorporate rotation of the tip, do offer improved performance on resistant tissue, because they require rotating seals and bearing they are complicated in construction, expensive to manufacture and fragile in use.

In 1969 Mitskevich described the development of, and experiments with, ultrasonic longitudinal-torsional resonators, known as L-T resonators. These ultrasonic devices are capable of transforming longitudinal motion into both longitudinal and torsional motion within one and same structure. Applications described by Mitskevich include welding and drilling. These resonators are also distinguished in converting imparted longitudinal motion from a transducer into both longitudinal and torsional motion at the tip of the L-T resonator. Such imparted longitudinal motion may be generated by any of the many common inexpensive electromechanical transducers for providing this motion by mechanical connection of such a transducer to the longitudinal torsional resonator. In 1981 Kleesatel (U.S. Pat. No. 4,281,987) connected a transducer providing longitudinal motion to an L-T resonator for the purpose of generating continuous rotary motion.

The resonators described by Mitskevich were made by creating an inhomogeneous cross section along the length of an otherwise uniform bar and then twisting the bar along its length. One way to create an inhomogeneous cross section to place grooves along the length of what was otherwise a round bar to create flutes. The resonator is then physically twisted about its axis, spiraling the grooves. The twisted bar is then connected to a transducer that produced longitudinal motion in response to application of an electrical current and voltage. The same structure can be obtained, and was evaluated by Mitskevich, by using a conventional twist drill or by machining the grooves into the bar. L-T resonators can also be made by twisting a bar containing a rectangular cross section about its axis to produce a spiral in exactly the way that drills were first made.

An L-T resonator containing a flat twisted section has the advantages of simplicity and economy in construction and can sustain greater torsional motion because the mass of the cross section remains uniformly distributed along its width. The mass of the cross section of the grooved twisted bar L-T resonator increases along its width or radius with the result that stress produced by torsional motion through the same angle is greater in this bar than in the flat twisted bar.

In 2000 Boukhny (U.S. Pat. No. 6,077,285) showed apparatus for providing both longitudinal and torsional ultrasonic tip for the purpose of enhancing tissue dissection. His device utilizes separate torsional and longitudinal transducers to provide this motion. As such, simultaneous operation of both transducers is described as providing both longitudinal and torsional motion of the working tip. However this system requires two electrical generators to supply the power, one each for each of the different transducers. Furthermore, all such devices, whether longitudinal, transverse or torsional must be fixed within an enclosure, such as a handpiece, preferably at points where there is no motion, known as motional nodes. However, because the wavelength of torsional and longitudinal vibration is, in general, substantially different, the node or nodes for longitudinal vibration and torsional motion will, in general, be located at different points on the transducer and other portions of other resonators attached to the transducers. Hence, in general, no true motionless point may be found with the result that either longitudinal or torsional motion will be communicated to the handpiece and thereby to the operator holding the handpiece. Although vibration isolators can be utilized to prevent the communication of such unintended motion, if they are truly isolating they invariably complicate construction of the device and, if simple, consume power in the form of heat generated by contact with a moving surface. Hence, Boukhn's device is both complicated to operate, needing two separate power sources, and difficult to construct.

BRIEF DESCRIPTION OF THE INVENTION

The invention described herein permits the efficacious dissection of tissue resistant to longitudinal or transverse vibration or a combination of longitudinal and transverse vibration by providing simultaneously longitudinal and torsional ultrasonic motion to a tissue contacting tip through the use of longitudinal-torsional resonators.

The invention has the further object of providing such longitudinal-torsional vibration using only one type of electromechanical transducer, either torsional or longitudinal and thereby simplifying the construction of ultrasonic dissection apparatus.

The invention has another object in permitting the application of longitudinal-torsional motion to tissue dissection using established, well-known and inexpensive electromechanical transducers heretofore developed for generating longitudinal motion.

Other objects, features and advantages of the invention will become apparent with reference to the drawings and the following description of the drawings, invention and claims.

BRIEF DESCRIPTON OF THE DRAWINGS

FIG. 2 is shaded isometric view of an example of an L-T knife tip ultrasonic dissector.

FIG. 3 is a shaded isometric view of an example of an L-T dissecting, and aspirating ultrasonic dissector.

FIG. 4 is an example of an ultrasonic L-T tissue dissector utilizing a torsional transducer and having a twisted section interposed between the transducer and the tip.

REFERENCE NUMERALS IN DRAWINGS

Figure 1:
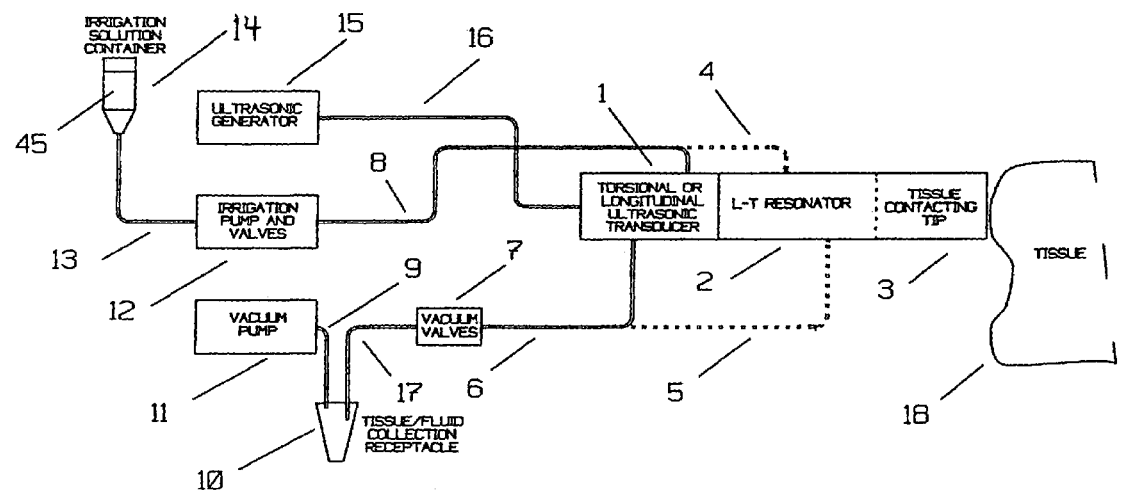
FIG. 1 is a block diagram illustrating the principal components of an ultrasonic tissue dissecting system incorporating L-T resonators.

1. Torsional or Longitudinal Ultrasonic Transducer
2. L-T Resonator
3. Tissue Contacting Tip
4. Irrigation Conduit to L-T Resonator
5. Vacuum Conduit to L-T Resonator
6. Vacuum conduit to Longitudinal or Torsional Ultrasonic Transducer
7. Vacuum Valves
8. Irrigation Conduit to Longitudinal or Torsional Ultrasonic Transducer
9. Vacuum Conduit to Tissue/Fluid Collection Receptacle
10. Tissue/Fluid Collection Receptacle
11. Vacuum Pump
12. Irrigation Pump and Valves
13. Irrigation Conduit to Irrigation Pump and Valves
14. Irrigation Solution Container
15. Ultrasonic Generator
16. Electrical Connection to Ultrasonic Longitudinal or Torsional Transducer
17. Vacuum Conduit to Vacuum Valves
18. Tissue
19. Ultrasonic Longitudinal Transducer
20. Voltage and Current applied to Ultrasonic Longitudinal Transducer
21. L-T resonator
22. Tissue contact point of L-T resonator
23. Transducer Longitudinal Motion
24. L-T motion at Tissue Contact point
25. Low motion region of Ultrasonic Longitudinal Transducer
26. Low motion region of L-T resonator
28. Coil
29. Magneto-strictive Longitudinal Electro-mechanical Transducer Element
33. Slot in L-T Resonator
34. Axial hole in L-T resonator
40. Torsional motion of Torsional Ultrasonic Transducer
41. Inhomogeneous portion of L-T resonator
42. Piezo-electric torsional elements
43. Electro-mechanical Torsional Transducer
44. Low motion region of Torsional Ultrasonic Transducer
45. Irrigation fluid
46. Piezo-electric longitudinal elements
47. First Electrical connection
48. Second Electrical connection

DETAILED DESCRIPTION OF THE INVENTION

The principal components of a system suitable for ultrasonic tissue dissection is shown in FIG. 1 along with their interconnection. Referring now to FIG. 1, an electromechanical transducer 1 that receives alternating electrical current and voltage through connections 16 from an ultrasonic generator 15 produces an alternating mechanical vibration at its point of mechanical contact with longitudinal torsional resonator 2. The longitudinal torsional resonator, receiving this vibration from the transducer by direct mechanical contact with transducer 1, produces in a tissue contacting tip longitudinal-torsional vibration. This tip 3 contacts tissue 18 for the purpose of dissection.

Electro-mechanical transducer 1 may produce either longitudinal or torsional motion in response to the supply of electrical energy. The tissue contacting tip 3 may be an integral part of the L-T resonator 2 or a separate, mechanically attached component.

Irrigation fluid 45 in container 14 is conveyed to either the transducer 1 or the L-T resonator 2 through a pump and valve control system 12 and conduits 13, 8 and 4 or other appliances suitable for fluid conveyance.

A vacuum pump 11 provides suction by connecting line 9 to a tissue and fluid receptacle 10 and thereby through connecting conduit 17 to control valves 7 and hence by connecting line 6 to the transducer or by connecting line 5 to the L-T resonator.

In operation, vibration, irrigation and suction may be present at the transducer or L-T resonator simultaneously, individually or in any combination.

The functions and utility of irrigation, suction which is also known as aspiration and vibration in dissecting tissue has been fully described by Banko (U.S. Pat. No. 3,589,363) and Broadwin (U.S. Pat. No. 4,136,700), both of which patents are incorporated herein by reference.

In FIG. 2 an electromechanical transducer 19 is shown mechanically connected to an L-T resonator 21 having an inhomogeneous cross sectional region 41 and mechanically joined to knife tissue contacting tip 22. The mechanical connection between the L-T resonator and the transducer and the L-T resonator and the tip may be made by any of the common methods known in the art such by screw threads, press fit, welding, brazing or the connection may be metallurgically continuous. Transducer 19 contains piezo-electric elements 46 which change their dimensions in response the application of an electric field and to which first and second connection wires 47 and 48, forming part of connections shown as 16 in FIG. 1 are attached. Transducer 19 produces, in response to the application of alternating current and voltage 20, a longitudinal vibration 23 at the point of connection to L-T resonator 26. The transducer 19 also possesses a rim 25 on which there is little or no vibration present and which therefore constitutes a region suitable for mounting or holding the transducer 19 in a stationary structure such as a handpiece. The L-T resonator may also contain a portion of its structure, shown as item 26, where there is also little or no mechanical vibration and which is again suitable for further securing it to a stationary object.

The L-T resonator converts the longitudinal vibration 23 into a longitudinal-torsional vibration 24 at tip 22. The ratio of the magnitude of the longitudinal-torsional vibration 24 to the longitudinal vibration 23, represented in FIG. 2 as the length of the double-ended arrow lines, may be any number greater than zero, but preferably lies in the range of 1 to 100.

Figure 2A:
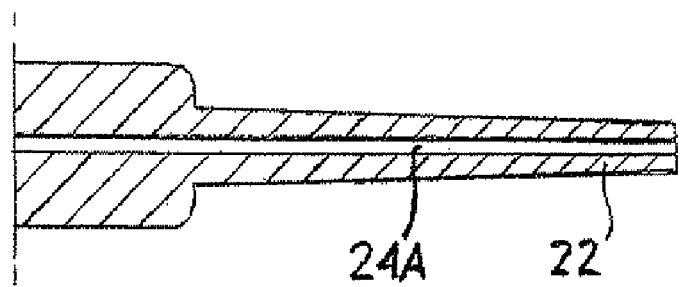
FIG. 2A is a longitudinal cross-sectional view of a portion of the tip shown in FIG. 2.

FIG. 2A illustrates the hollow longitudinal passageway 24A in the tip 22.

As Mitskevich has described, for the L-T resonator 21 to produce a torsional component of motion comparable to the longitudinal component a substantial portion, shown as item 41 in the drawings, of the cross sectional mass must be made inhomogeneous. If this inhomogeneity is made by twisting a flat bar or grooving a round one, this inhomogeneity should preferentially made in the portion of the bar subjected to maximum stress. As previously referenced, to minimize the stress produced in the inhomogeneous portion of the resonator, in the preferred embodiment of this invention, the inhomogeneity is created by twisting a bar of rectangular cross section about its axis. Normally this portion of the bar can be found using the stress distribution that would take place if the bar were not twisted. Such stress distributions have been described by Frederick and are available to practitioners skilled in the art. In addition, as Mitskevich has shown, an L-T resonator made by twisting a bar may be joined to another untwisted bar having a larger cross sectional area than the twisted bar to form a stepped half wavelength resonator as described by Wuchinich (U.S. Pat. No. 5,811,909). In such a construction, a connection made to the transducer at the available end of the untwisted bar will produce at the end of the twisted bar longitudinal-torsional motion greater in magnitude than that at the point of contact with the transducer.

The portion of the resonator containing the cross sectional inhomogeneity may also be tapered, as shown in FIG. 2, from a larger cross section at the end connecting to the transducer to a smaller cross section at the opposite end to again produce an increase in the longitudinal and torsional components of motion. Frederick has also described a variety of tapers suitable for the purpose and known in the art.

It also possible to create the inhomogeneity necessary to produce longitudinal-torsional vibration from a longitudinal or torsional vibration by making the material of the bar itself inhomogeneous. For example, if the density or elasticity of the bar is made to vary in a helical manner along the length of the bar, longitudinal or torsional vibration at one end of the bar will be converted in to longitudinal-torsional vibration at the other end.

To both dissect and aspirate tissue, the L-T resonator may be made with a hollow passage that communicates with a similar hollow passage in the transducer or with a fitting attached to tubing or other tissue and fluid carrying devices.

In FIG. 3 an electromechanical transducer 19 is mechanically attached to an L-T resonator 21. The transducer 19 contains a magnetostrictive element 29 which changes its dimensions in response to the application of a magnetic and which vibrates longitudinally with magnitude and direction shown as item 23 in response to a voltage and current 20 applied to coil 28 which generates the magnetic field. The portion 41 of the L-T resonator that contains an inhomogeneous cross section also contains a hole 34 through its length which communicates with slot 33, thereby permitting connections in the slot to fluid lines 4 or 5 of FIG. 1 to either a source of irrigation fluid or suction as shown by Banko (U.S. Pat. No. 3,589,363) and Wuchinich (U.S. Pat. No. 4,063,557) which are herein incorporated by reference. Wuchinich also shows an alternative fluid connection to the transducer (U.S. Pat. No. 4,750,902) again incorporated herein by reference. The tissue contacting tip part of, or attached to, the L-T resonator 22 vibrates longitudinally and torsionally with a magnitude 24 shown. The ratio of the vibration magnitude 24 to the transducer magnitude 23, taken as the ratio of the lengths of respective double arrowhead lines, can be any value greater than 0, but preferably lies within the range of 1 and 100.

FIG. 4 shows an electromechanical torsional transducer 43 mechanically joined to an L-T resonator 21 having a knife tissue contacting tip 22. Transducer 43 contains piezoelectric elements 42 to which first and second connecting wires 47 and 48 respectively, forming part of the connections identified as item 16 in FIG. 1, are attached. Transducer 43 produces, in response to the application of alternating current and voltage 20, a torsional vibration 40 at the point of connection to the L-T resonator. The transducer 43 also possesses a rim 44 on which there is little or no vibration present and which therefore constitutes a region suitable for mounting or holding the transducer 43 in a stationary structure such as a handpiece. The L-T resonator contains a section with an inhomogeneous cross sectional portion 41 between two sections of uniform cross section. The tissue contacting portion 22 of the L-T resonator 21 executes, in response to the torsional vibration 40 produced by transducer 43 a longitudinal-torsional vibration 24. The ratio of this vibration to that of the transducer, taken as the length of the double ended arrowhead line may be any value greater than 0, but preferably lies within the range of 1 and 100.

While specific embodiments of the present invention have been described above, these examples are given to explain the general construction of the invention and its operation. Many variations in design of L-T ultrasonic tissue dissectors are possible, including changes in materials, transducers, geometry and tips all known to persons skilled in the art. Such variations may be made without departure from the scope or spirit of this invention.

What is claimed is:

1. An ultrasonic longitudinal-torsional tissue dissection system having only a single source of vibration consisting of only a single electro-mechanical transducer for receiving alternating electrical current and voltage from an ultrasonic generator, said transducer having a point of mechanical contact with a resonator, said transducer producing at said point of contact only a single type of vibration selected from the group consisting of longitudinal vibration and torsional vibration, said transducer immediately upstream from said point of mechanical contact having only said single type of vibration, said resonator being mechanically joined to a tip shaped for cutting biological tissue, a hollow longitudinal passageway extending completely through said tip and into said resonator, and at least a portion of said resonator having a helical spiral formation in its outer surface which creates an inhomogeneous cross section which at said resonator converts the single type of vibration into a combined longitudinal-torsional vibration upstream from said tip for imparting the longitudinal-torsional vibration to said tip.

2. A system of claim 1 where said inhomogeneous portion comprises a grooved round bar.

3. A system of claim 1 where said tip has a cutting edge.

4. A system of claim 1 where a source of irrigation is connected to said passageway.

5. A system of claim 1 where a vacuum source is connected to said passageway.

6. A system of claim 1 where a slot is in said resonator communicating with said passageway, and an external flow line in flow communication with said slot.

7. A system of claim 1 where said single type of vibration is longitudinal.

8. A system of claim 1 where said single type of vibration is torsional.

9. A system of claim 1 where the ratio of longitudinal-torsional vibration at said tip to the single type of vibration at said point of mechanical contact of said transducer with said resonator is in the range of 1 to 100.

10. A system of claim 1 where said inhomogeneous portion is tapered from a larger cross nearer to said transducer to a smaller cross section nearer to said tip.

11. An ultrasonic longitudinal-torsional tissue dissection system having only a single source of vibration consisting of only a single electro-mechanical transducer for receiving alternating electrical current and voltage from an ultrasonic generator, said transducer having a point of mechanical contact with a resonator, said transducer producing at said point of contact only a single type of vibration selected from the group consisting of longitudinal vibration and torsional vibration, said transducer immediately upstream from said point of mechanical contact having only said single type of vibration, said resonator being mechanically joined to a tip shaped for cutting biological tissue, a hollow longitudinal passageway extending completely through said tip and into said resonator, and at least a portion of said resonator having being a round bar which is grooved and creates an inhomogeneous cross section which at said resonator converts the single type of vibration into a combined longitudinal-torsional vibration upstream from said tip for imparting the longitudinal-torsional vibration to said tip.

12. The system of claim 11 where said round bar is grooved by having a plurality of longitudinally extending spiral grooves.

13. A system of claim 11 where a source of irrigation is connected to said passageway.

14. A system of claim 11 where a vacuum source is connected to said passageway.

* * * * *